(12) United States Patent
Bachmann et al.

(10) Patent No.: US 10,463,612 B2
(45) Date of Patent: *Nov. 5, 2019

(54) METHOD FOR MANUFACTURING MEDICATED CHEWING GUM WITHOUT COOLING

(71) Applicant: MastiX, LLC, Jupiter Island, FL (US)

(72) Inventors: Lisa Bachmann, Forest Hill, MD (US); Robert Estey, Hunt Valley, MD (US)

(73) Assignee: Per Os Biosciences LLC, Hobe Sound, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/622,632

(22) Filed: Jun. 14, 2017

(65) Prior Publication Data

US 2017/0281539 A1   Oct. 5, 2017

Related U.S. Application Data

(62) Division of application No. 14/732,072, filed on Jun. 5, 2015, now Pat. No. 9,744,128.

(60) Provisional application No. 62/008,211, filed on Jun. 5, 2014.

(51) Int. Cl.
| | |
|---|---|
| A61K 9/68 | (2006.01) |
| A23G 4/10 | (2006.01) |
| A23G 4/08 | (2006.01) |
| A61K 31/352 | (2006.01) |
| A61K 31/05 | (2006.01) |
| A23G 4/06 | (2006.01) |
| A23G 4/12 | (2006.01) |
| A61K 31/522 | (2006.01) |
| A61K 31/722 | (2006.01) |
| A61K 36/185 | (2006.01) |
| A23G 4/18 | (2006.01) |

(52) U.S. Cl.
CPC ........... *A61K 9/0058* (2013.01); *A23G 4/066* (2013.01); *A23G 4/068* (2013.01); *A23G 4/08* (2013.01); *A23G 4/10* (2013.01); *A23G 4/12* (2013.01); *A61K 31/05* (2013.01); *A61K 31/352* (2013.01); *A61K 31/522* (2013.01); *A61K 31/722* (2013.01); *A61K 36/185* (2013.01); *A23G 4/18* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,370,350 A | 1/1983 | Fisher et al. | |
| 4,753,805 A | 6/1988 | Cherukuri et al. | |
| 4,975,270 A | 12/1990 | Kehoe | |
| 5,711,961 A | 1/1998 | Reiner et al. | |
| 5,866,179 A | 2/1999 | Testa | |
| 6,322,828 B1 * | 11/2001 | Athanikar | A23G 4/00 424/440 |
| 6,344,222 B1 | 2/2002 | Cherukuri et al. | |
| 6,582,738 B2 | 6/2003 | Gubler | |
| 7,101,579 B2 | 9/2006 | Athanikar et al. | |
| 7,208,186 B2 | 4/2007 | Norman et al. | |
| 7,351,438 B2 | 4/2008 | Sozzi et al. | |
| 7,815,898 B2 | 10/2010 | Savica | |
| 9,023,322 B2 | 5/2015 | Van Damme et al. | |
| 9,433,601 B2 | 9/2016 | Van Damme et al. | |
| 9,744,128 B2 * | 8/2017 | Bachmann | A61K 9/0058 |
| 2004/0028772 A1 | 2/2004 | Andersen | |
| 2004/0194793 A1 | 10/2004 | Lindell et al. | |
| 2005/0090468 A1 | 4/2005 | Jarvinen et al. | |
| 2006/0003050 A1 * | 1/2006 | Nissen | A23G 3/004 426/3 |
| 2006/0045934 A1 | 3/2006 | Kabse et al. | |

(Continued)

FOREIGN PATENT DOCUMENTS

| | | | | |
|---|---|---|---|---|
| EP | 0151344 A2 * | 8/1985 | ............... | A23G 4/06 |
| WO | 2006010939 A1 | 2/2006 | | |

(Continued)

OTHER PUBLICATIONS

Barbora Vraníková and Jan Gajdziok. Liquisolid systems and aspects influencing their research and development. Acta Pharm. 63 (2013) 447-465. (Year: 2013).*

(Continued)

*Primary Examiner* — Michael P Cohen
(74) *Attorney, Agent, or Firm* — Mintz Levin Cohn Ferris Glovsky and Popeo, P.C.; Nicholas A. Zachariades

(57) ABSTRACT

An improved method for manufacture of chewing gums containing active ingredient(s) that preserves the efficacy of the active ingredient(s) by avoiding exposure to high heat and extreme cold during milling that can otherwise degrade the active's efficacy. A chewing gum base is used, along with one or more therapeutically-active ingredients, one or more sweeteners (alcohol-based and/or natural), and one or more flavorings and optional flavor modifiers. The method generally comprises heating the gum base in ovens to melt the gum base. Separately, the active ingredient(s), sweeteners and flavorings are combined in a mixer. The melted gum base is added to the mixer and cools to produce a particulate mixture. As mixing continues the mass cools to room temperature and forms granular pieces. The granular pieces are ground into a powder at room temperature, mixed at room temperature with tableting excipients, and tableted. Several variations on the foregoing are also described.

10 Claims, 8 Drawing Sheets

(56) References Cited

U.S. PATENT DOCUMENTS

| | | | |
|---|---|---|---|
| 2006/0115433 A1 | 6/2006 | Andersen et al. | |
| 2006/0147580 A1 | 7/2006 | Nissen et al. | |
| 2006/0188465 A1 | 8/2006 | Perrier et al. | |
| 2011/0070286 A1* | 3/2011 | Hugerth | A61K 9/0058 424/440 |
| 2016/0354310 A1 | 12/2016 | Bachmann et al. | |
| 2017/0273902 A1 | 9/2017 | Bachmann et al. | |
| 2017/0273903 A1 | 9/2017 | Bachmann et al. | |

FOREIGN PATENT DOCUMENTS

| | | |
|---|---|---|
| WO | 2006050314 A2 | 5/2006 |
| WO | 2009120080 A1 | 10/2009 |

OTHER PUBLICATIONS

Sigma-Aldrich Particle Size Conversion Table (Downloaded Nov. 12, 2014 from www.sigmaaldrich.com; full address is in the Rejection. (Year: 2014).*

Wikipedia article "Sugar substitute" at https://en.wikipedia.org/wiki/Sugar_substitute. Downloaded Jan. 2, 2019) (Year: 2019).*

Welti-Chanes, J. et al. Phase Trasitions and hygroscopicity in chewing gum manufacture. In Food Engineering: Integrated Approaches Editors: Gutiérrez-Lopez, Gustavo F., Welti-Chanes, Jorge, Parada-Arias, Efrén (Es.) Springer 2008. (Year: 2008).*

Reichard "CanChew Biotechnologies CBD-Infused Chewing Gum", dated Aug. 30, 2013, downloaded Nov. 27, 2016, from the site: https://www.medicaljane.com/2013/08/30/canchew-biotechnologies-cbd-infused-chewing-gum/) (Year: 2013).*

Saddique "Pakistan's Goat-Grown Hashish," downloaded Jan. 2, 2019 from the website of Radio Free Europe/ Radio Liberty at: https://www.rferl.org/a/pakistan-hashish-goat-sheep-skin-tirah-maidan-awal-namber-gada/24601598.html; dated Jun. 2, 2012. (Year: 2012)*

Chaudhary et al. (2012) "Directly compressible medicated chewing gum formulation for quick relief from common cold," International journal of pharmaceutical investigation. 2(3):123-133.

Devinsky et al. (Jun. 2014) "Cannabidiol: Pharmacology and potential therapeutic role in epilepsy and other neuropsychiatric disorders," Epilepsia. 55(6):791-802. [23 pages].

Jacobsen et al. (Jun. 2004) "Medicated chewing gum pros and cons," American Journal of Drug Delivery. 2(2):75-88.

Zhang et al. (2002) "Oral mucosal drug delivery," Clinical pharmacokinetics. 41(9):661-680.

* cited by examiner

METHOD FOR MANUFACTURING MEDICATED CHEWING GUM WITHOUT COOLING

CROSS-REFERENCE TO RELATED APPLICATIONS

In accordance with 37 CFR § 1.76, a claim of priority is included in an Application Data Sheet filed concurrently herewith. Accordingly, the present invention claims priority as a divisional of U.S. patent application Ser. No. 14/732,072, entitled "METHOD FOR MANUFACTURING MEDICATED CHEWING GUM WITHOUT COOLING", filed Jun. 5, 2015, which claims priority to U.S. Provisional Patent Application No. 62/008,211, filed Jun. 5, 2014.

BACKGROUND OF THE INVENTION

1. Field of the Invention

The present invention relates generally to the manufacture of chewing gums containing active ingredients and, more specifically, to a method for manufacture of such chewing gums that preserves the efficacy of the active ingredient(s).

2. Description of the Background

The conventional methods of producing compressible chewing gums entail freezing the gum base and then grinding to obtain a particulate material, mixing the particulate material with other materials (usually in particulate form), then pressing the compressible chewing gum mixture into tablets.

For example, U.S. Pat. No. 4,370,350 to Fisher et al. (Wrigley) issued Jan. 25, 1983 shows a method for the manufacture of chewing gum in which the viscosity of the gum base is first reduced by heating. A bulking agent is then added to the gum base while mixing. The mixture is cooled during mixing to form granules. More bulking agent is added to form layers around the granules, and there is no active ingredient nor any grinding or tableting.

For example, U.S. Pat. No. 7,101,579 to Athanikar et al. (Deseret Labs) issued Sep. 5, 2006 shows a chewing gum composition containing an active ingredient. The gum base is cooled to a temperature at which the composition is brittle, ground, mixed with the active ingredient as desired, and formed into a tablet.

U.S. Pat. No. 5,711,961 to Reiner et al. (APR Applied Pharma) issued Jan. 27, 1998 discloses a pharmaceutical chewing gum composition in tablet form made by freezing, grinding the gum in a mill, and granulating the ground gum in a fluid bed. Thereafter, a medicinal active agent is mixed with the granulate, and the granulates are compressed into tablets. This patent is provided for general interest.

U.S. Pat. No. 4,975,270 to Kehoe (Nabisco) issued 4 Dec. 1990 shows a medicament-active chewing gum made by freezing and grinding into a particle. Note that the gum and the active ingredient are mixed together while heating, and then the mixture is frozen and ground into particles.

U.S. Pat. No. 6,582,738 to Gubler (Deseret Laboratories) issued Jun. 24, 2003 shows a process for preparing chewing gum containing a nutritional supplement that includes cooling and grinding the cooled, brittle gum composition to form a chewing gum powder, mixing with an active nutritional supplement, granulating, and then compressing the granules to form chewing gum tablets. The chewing gum composition is cooled to a temperature at which the gum composition is brittle.

Alternatively it is known to mix a powder sweetener into a molten gum base while subjecting the mixture to shear (i.e., through the mixing force) and cooling. This technique causes the grinding as the mixture becomes more rigid due to cooling and the addition of the dry sweetener.

U.S. Pat. No. 4,753,805 to Cherukuri et al. (Warner-Lambert) issued Jun. 28, 1988 shows a tabletted chewing gum composition and method of preparation in which a gum base is mixed with a sweetener, and the mixture is ground with an abrasive grinding aid (alkali metal phosphates, alkaline earth metal phosphates, maltodextrins).

U.S. Pat. No. 7,208,186 (SPI Pharma, Inc.) to Norman et al. issued Apr. 24, 2007 shows a chewing gum formulation with an active ingredient. The gum base, granulating agent and a processing aid are mixed until in particulate form. The temperature in the mixer is then increased to a temperature which is sufficient to melt at least the surface of the gum base particles and the contents of the mixer are mixed for several minutes at this temperature to obtain a uniform mixture of the gum base, the granulating agent and the processing aid in particulate form particles inside the mixer. Next, the active ingredient is added to the particles and most or all of the active ingredient is loosely bound to the outer surfaces of the particles. The particles are tabletted. There is no cooling necessary to make the chewing gum formulation friable.

U.S. Pat. No. 7,351,438 to Sozzi et al. (Gum Base Co., SPA) issued Apr. 1, 2008 shows a method of preparing chewing gum in tablet form by direct compression of the chewing gum formulation in powder form. The chewing gum in powder form is produced by a method which comprises the following steps:

a) mixing of a soft basic gum with at least one sweetener and, optionally, at least one other typical chewing-gum ingredient, at a temperature of between 35 and 75° C., b) cooling of the mixture thus obtained to a temperature of between 0 and −40° C. and preferably between −10 and −40° C., c) grinding and subsequent screening of the mixture thus obtained to a particle size of less than 10 mesh, d) optional mixing of the powder thus obtained with at least one anti-agglutination agent, e) optional compression of the mixture thus obtained.

U.S. Pat. No. 5,866,179 to Testa (Avant-Garde Technologies) issued Feb. 2, 1999 shows a medicated chewing gum and a process for preparation thereof in which the active agent is mixed with a granulated gum base under controlled temperature and humidity and the blended components are cold-pressed to produce a final gum product. The gum base is prepared by cooling natural gum to −10 degree C., then grinding it. It is noted that the elevated temperatures used in the melt can adversely affect the chemical stability of the therapeutic agent.

Neither prior method is optimal for chewing gums with active ingredients since heating and/or cooling can erode the effectiveness of the active. The proposed process avoids this by initially heating a gum base to slightly elevated internally measured temperature between 140-160 deg. F. in ovens, mixing with the active as it cools to produce a particulate mixture, grinding into compressible powder, then forming into tablets. The temperature of the gum base exceeds that of the mixer when first introduced, but as mixing continues it cools and mixes into a particulate form=inside the mixer. Next, the particulate is ground into compressible powder at room temperature, mixed at room temperature with excipients, and tabletted. This avoids heating/cooling of the active and preserves its efficacy.

SUMMARY OF THE INVENTION

It is an object of the invention to provide an improved method for manufacture of chewing gums containing active ingredients that preserves the efficacy of the active ingredient(s).

It is another object to provide a method for manufacture of chewing gums containing active ingredients that avoids exposure of the active ingredients to high heat during mixing that can degrade the active's efficacy.

It is another object to provide a method for manufacture of chewing gums containing active ingredients that avoids exposure of the active ingredients to extreme cold during milling that can degrade the active's efficacy.

It is another object to provide a method for manufacture of chewing gums containing active ingredients in which the active in oil form can be mixed directly into the other powder ingredients and tableted, rather than spray-dried onto a powder carrier for tableting as with the prior art methods. This direct mixing of the oil into the powder can deliver more active ingredient with less weight than the alternatives thus making the tableting process more efficient and less expensive In accordance with the foregoing objects, present invention provides an improved method for manufacture of chewing gums containing active ingredients that preserves the efficacy of the active ingredient(s) by avoiding exposure to high heat and extreme cold during milling that can otherwise degrade the active's efficacy. A suitable chewing gum base is used preferably comprising one or more constituents including elastomers for elasticity, resins to act as binders and softeners, plasticizers to render the elastomer soft to ensure thorough blending of the gum base, fillers contributing to the overall texture, and antioxidants to prevent oxidation of the gum base and flavors during shelf life. In addition, one or more therapeutically-active ingredients are used, one or more sweeteners (alcohol-based and/or natural), and one or more flavorings and optional flavor modifiers are used.

Generally, the method comprises initially heating the gum base in ovens to melt the gum base to an internally measured temperature between 140-160 deg. F. Separately, powdered ingredients including one or more active ingredient(s), sweeteners and flavorings are combined in a mixer. The melted gum base is added to the mixer and cools to produce a particulate mixture. The temperature of the gum base exceeds that of the mixer when first introduced, but as mixing continues it cools quickly to room temperature and forms granular pieces. The granular pieces are conditioned for a period of time. Conditioning is the time between the mixing and grinding of the gum. Conditioning allows the granular pieces to dry slightly and complete the crystallization process. Next, the granular pieces are ground into a powder at room temperature, mixed at room temperature with tableting excipients, and tableted. This process avoids extreme heating or cooling of the active ingredient(s) and preserves the efficacy.

The present invention including several embodiments is described in greater detail in the detailed description of the invention, and the appended drawings. Additional features and advantages of the invention will be set forth in the description that follows, will be apparent from the description, or may be learned by practicing the invention.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENT

Figure 1:
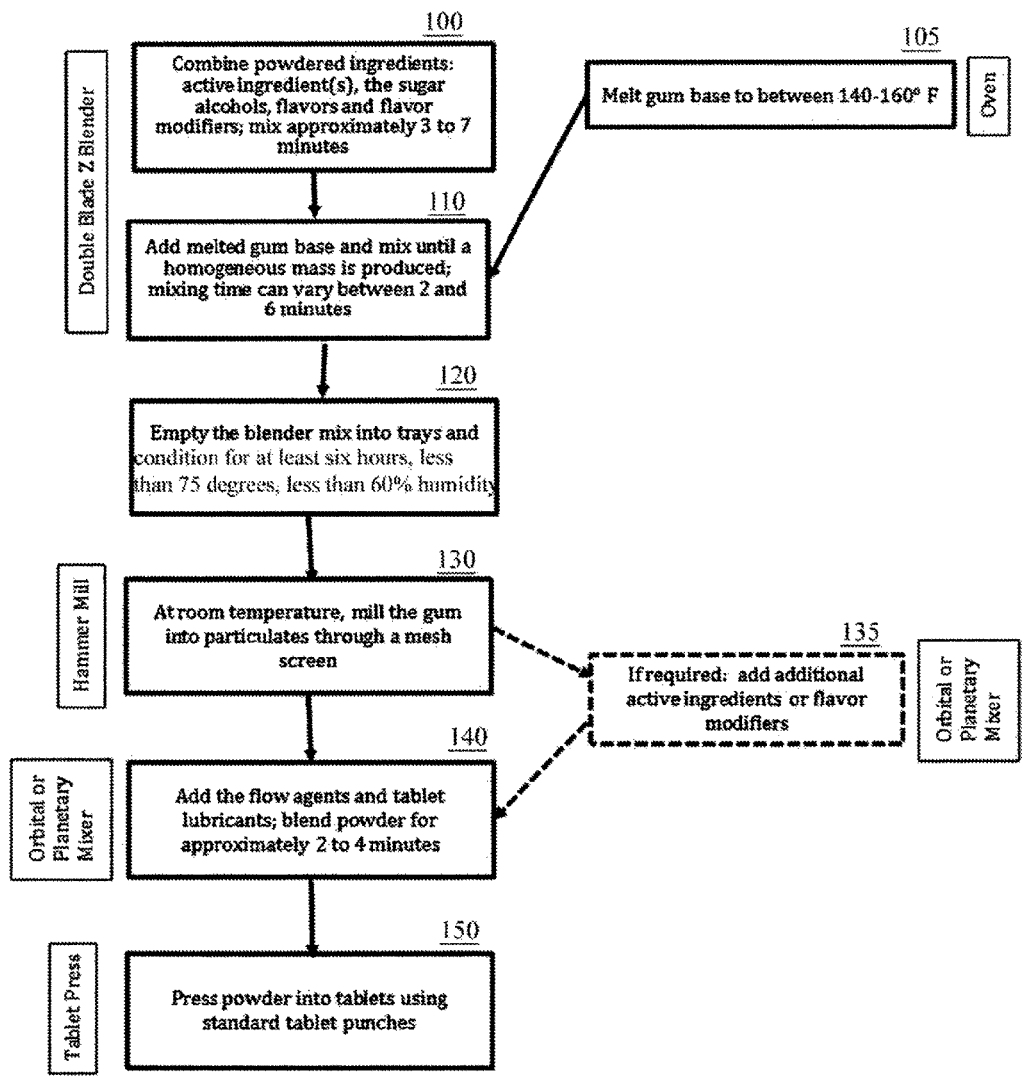
FIG. 1 is a process flow diagram of a first embodiment of the method for manufacturing chewing gum according to the invention, suited for active ingredient(s) that are provided in powder form.

Reference will now be made in detail to preferred embodiments of the present invention, examples of which are illustrated in the accompanying drawings. Wherever possible, the same reference numbers will be used throughout the drawings to refer to the same or like parts.

For purposes of description, the term "active" is herein defined as the ingredient or ingredients that provide a therapeutic effect. In the present invention active(s) may be provided in either powder or oil form. An active in oil form is defined as a free flowing liquid, semi-solid, or paste that is lipid-based and not water soluble. In the case of a semi-solid or paste, when heated to a maximum temperature of 140 deg. F., the material changes to an oil. Active ingredients in oil form can include hemp oil, THC resin, any cannabinoid oil, as well as pharmaceutical actives, botanicals and essential oils.

The invention generally is an improved method for manufacture of chewing gums containing active ingredients that preserves the efficacy of the active ingredient(s) by avoiding exposure to high heat and extreme cold, mainly during milling, that can otherwise degrade the active's efficacy. A suitable chewing gum base is used comprising one or more constituents including elastomers for elasticity, resins to act as binders and softeners, plasticizers to render the elastomer soft to ensure thorough blending of the gum base, fillers contributing to the overall texture, and antioxidants to prevent oxidation of the gum base and flavors during shelf life.

Generally, the method comprises initially heating the gum base in ovens to melt the gum base to an internally measured temperature between 140-160 deg. F. Ingredients, including one or more active ingredient(s), are combined in a mixer. The melted gum base is added to the mixer and cools to produce a particulate mixture. The temperature of the gum base exceeds that of the mixer when first introduced, but as mixing continues it cools quickly to room temperature and forms rock-sized granular pieces. These granular pieces are then conditioned for a period of time, which allows the granular pieces to dry slightly and complete the crystallization process. Preferably, the pieces are conditioned for at least 6 hours at a temperature not greater than 75 deg. F. and 60% relative humidity. Next, the pieces are ground into a powder at room temperature, mixed at room temperature with tableting excipients, and tableted. This avoids extreme heating or cooling of the active ingredient(s) and preserves the efficacy.

The active ingredients may be provided in raw powder or oil form, and the present application suggests two alternative methods one suited for the powder form and one for the oil form. When the active ingredient(s) is in oil form, the oil can be mixed directly into the other powder ingredients and tableted, and there is no need for spray-drying the oil onto a powder carrier for tableting as with the prior art methods. This direct mixing delivers more active ingredient with less weight thus making the tableting process more efficient and less expensive.

FIG. 1 is a flow diagram of the method for manufacturing chewing gum according to an embodiment of the invention suited for active ingredient(s) in powder form.

At step 105 one or more different gum base(s) are placed in trays lined with a sugar alcohol and the trays are placed in an oven. The gum base is melted until it reaches an internally measured temperature between 140-160 deg. F. Temperature may be measured with a commercial food thermometer.

At step 100, in a commercial mixer, preferably a double Z-blade mixer (for example, a Winkworth® double blade Z blender), the active ingredient(s), the sugar alcohols, flavors and flavor modifiers are added and mixed approximately 3 to 7 minutes.

At step 110 the melted gum base is added into the mixer and mixed until a homogeneous mass is produced. The mixing time may vary within a range of from 2 to 6 minutes.

At step 120 the mass is removed from the blender and conditioned in trays for a minimum of 6 hours at a temperature not greater than 75 deg. F. and 60% relative humidity.

At step 130, after the conditioning period, the gum is milled into particulates at room temperature using a hammer mill that forces the particulates through a mesh screen of appropriate predetermined particle size ranging between 0.10 inch to 0.30 inch with an optimal size of 0.24 inch.

Optionally, at step 135 other active ingredients, flavor modifiers, or the like may be added.

At step 140 the resulting powder is placed in an orbital or planetary mixer and the flow agents and tablet lubricants are added. The powder is blended for approximately 2 to 4 minutes.

At step 150 the powder is tableted using standard tablet punches on any suitable commercial tablet press.

The foregoing method entirely avoids exposure of the active ingredient to high heat or extreme cold during milling that would otherwise degrade the active's efficacy.

Figure 2:
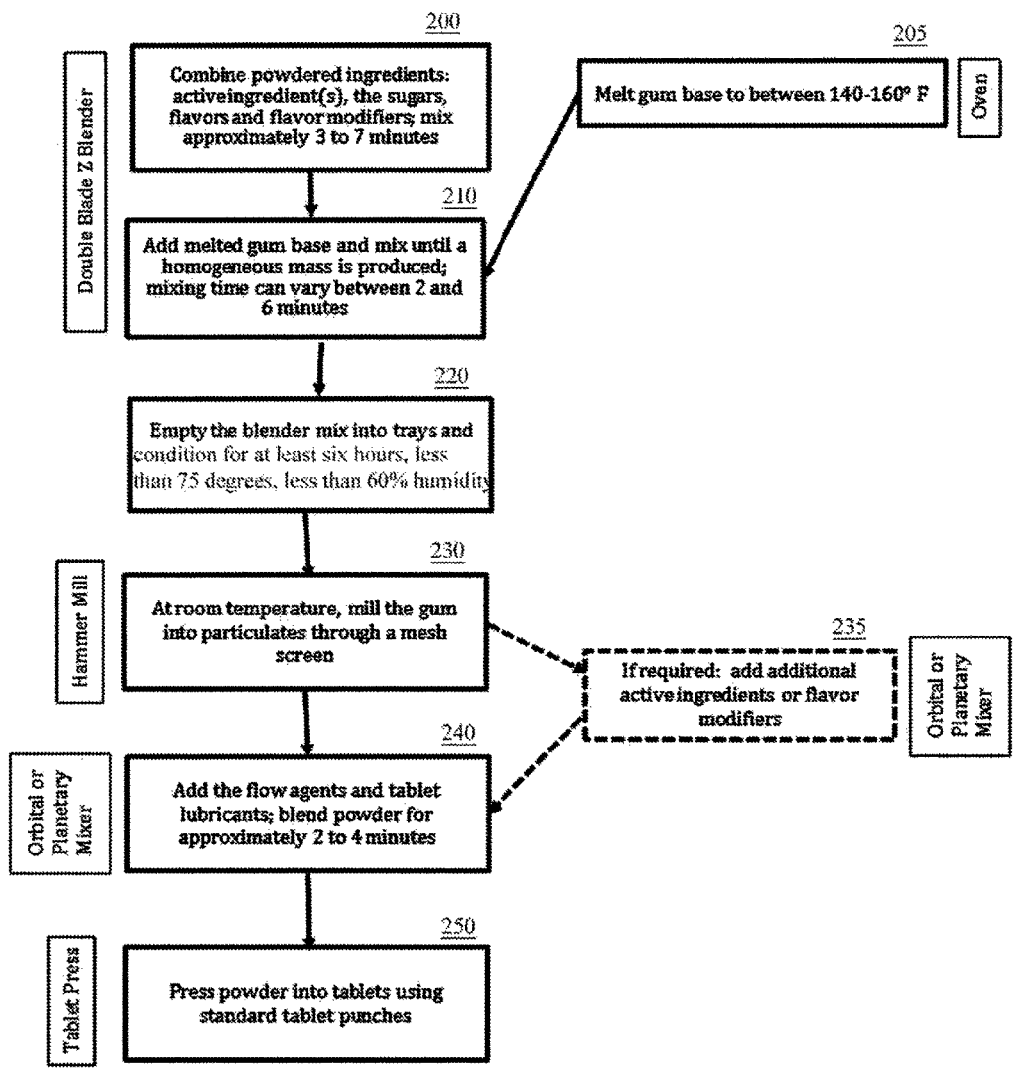
FIG. 2 is a process flow diagram of a second embodiment of a method for manufacturing chewing gum according to the invention, likewise suited for active ingredient(s) that are provided in powder form.

FIG. 2 is a flow diagram of the method for manufacturing chewing gum according to another embodiment of the invention, also suited for active ingredient(s) in powder form.

At step 205 one or more different gum base(s) are placed in trays lined with a sugar and the trays are placed in an oven. The gum base is melted until it reaches an internally measured temperature between 140-160 deg. F.

At step 200, in a commercial mixer, preferably a double Z-blade mixer (for example, a Winkworth® double blade Z blender), the active ingredient(s), the sugars, flavors and flavor modifiers are added and mixed approximately 3 to 7 minutes.

At step 210 the melted gum base is added into the mixer and mixed until a homogeneous mass is produced. The mixing time may vary within a range of from 2 to 6 minutes.

At step 220 the mass is removed from the blender and conditioned in trays for a minimum of 6 hours at a temperature not greater than 75 deg. F. and 60% relative humidity.

At step 230, after the conditioning period, the gum is milled into particulates at room temperature using a hammer mill that forces the particulates through a mesh screen of appropriate particle size ranging between 0.10 inch to 0.30 inch with an optimal size of 0.24 inch.

Optionally, at step 235 other active ingredients, flavor modifiers, or the like may be added.

At step 240 the resulting powder is placed in an orbital or planetary mixer and the flow agents and tablet lubricants are added. The powder is blended for approximately 2 to 4 minutes.

At step 250 the powder is tableted using standard tablet punches on any suitable commercial tablet press.

The foregoing method entirely avoids exposure of the active ingredient to high heat or extreme cold during milling that would otherwise degrade the active's efficacy.

Figure 3:
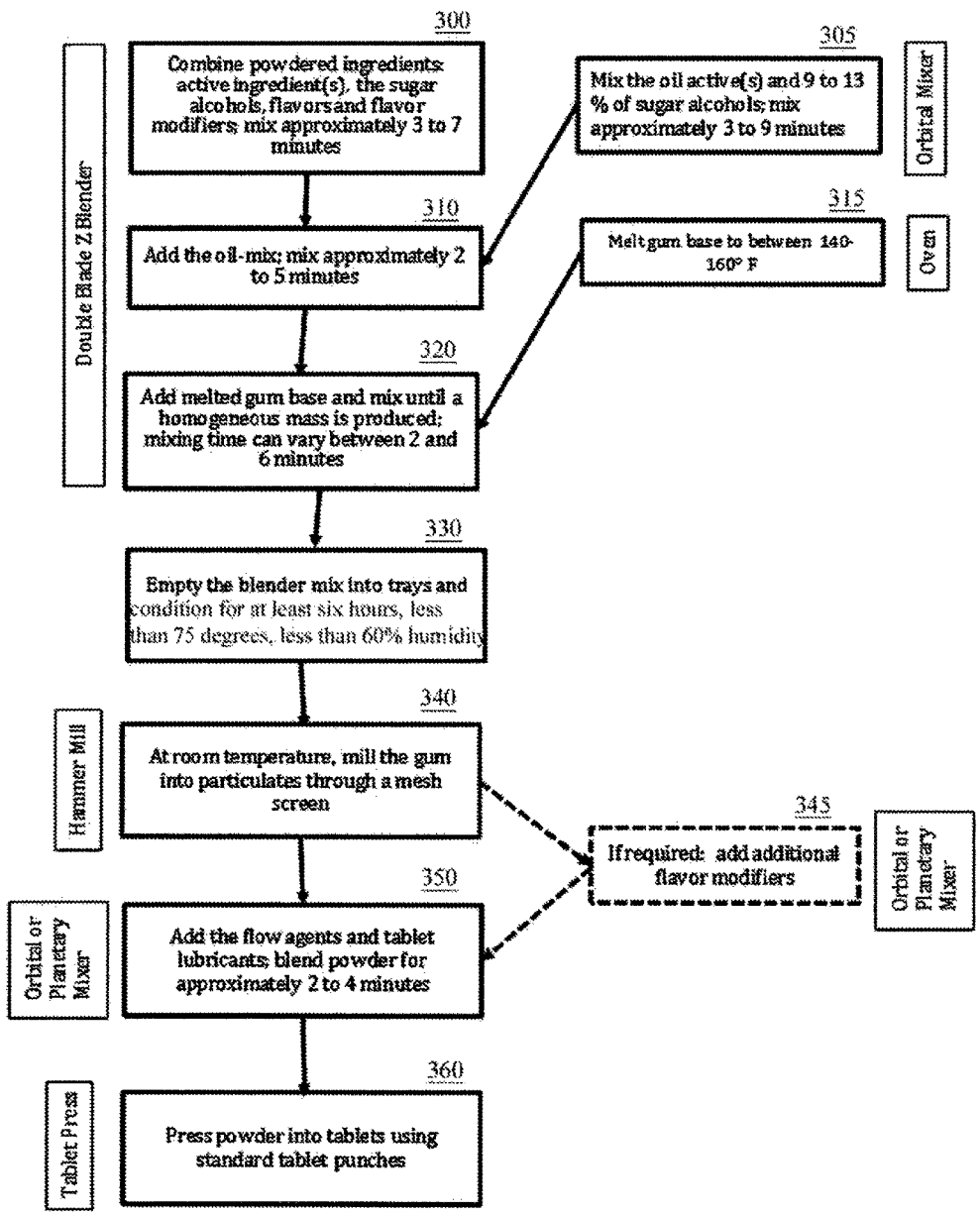
FIG. 3 is a process flow diagram of a third embodiment of the method for manufacturing chewing gum according to the invention, suited for active ingredient(s) that are provided in oil form.

FIG. 3 is a flow diagram of a method for manufacturing chewing gum according to an alternate embodiment of the invention suited for active ingredient(s) that are provided in oil form.

At step 305 a pre-mix consisting of the active(s) and a portion of the sweeteners comprising approximately 9 to 13% of one or more sugar alcohols (see Table 1, 3, 5, 6 below) are mixed in a suitable commercial orbital mixer. These ingredients are mixed approximately 3 to 9 minutes, until a homogeneous mix is obtained.

Separately, at step 300 in a double blade Z blender, the balance of the sweeteners (the remaining 87-91% of the sugar alcohol(s), plus the flavors and flavor modifiers are added and mixed approximately 3 to 7 minutes.

At step 310 the premix containing the active oil(s) is added to the blender and is mixed approximately 2 to 5 minutes.

At step 315 one or more different gum base(s) are placed in trays lined with a sugar alcohol and the trays are placed in an oven. The gum base is melted until it reaches an internally measured temperature between 140-160 deg. F.

At step 320 the melted gum base is added into the mixer and mixed until a homogeneous mass is produced. The mixing time may vary within a range of from 2 to 6 minutes.

At step 330 the mass is removed from the blender and conditioned in trays for a minimum of 6 hours at a temperature not greater than 75 deg. F. and 60% relative humidity.

At step 340, after the conditioning period, the gum is milled into particulates at room temperature using a hammer mill that forces the particulates through a mesh screen of appropriate pre-determined particle size ranging between 0.10 inch to 0.30 inch with an optimal size of 0.24 inch.

Optionally, at step 345 flavor modifiers may be added.

At step 350 the resulting powder is placed in an orbital or planetary mixer and the flow agents and tablet lubricants are added. The powder is blended for approximately 2 to 4 minutes.

At step 360 the powder is tableted using standard tablet punches on any suitable commercial tablet press.

As above this method entirely avoids exposure of the active ingredient to high heat or extreme cold during milling that would otherwise degrade the active's efficacy.

Figure 4:
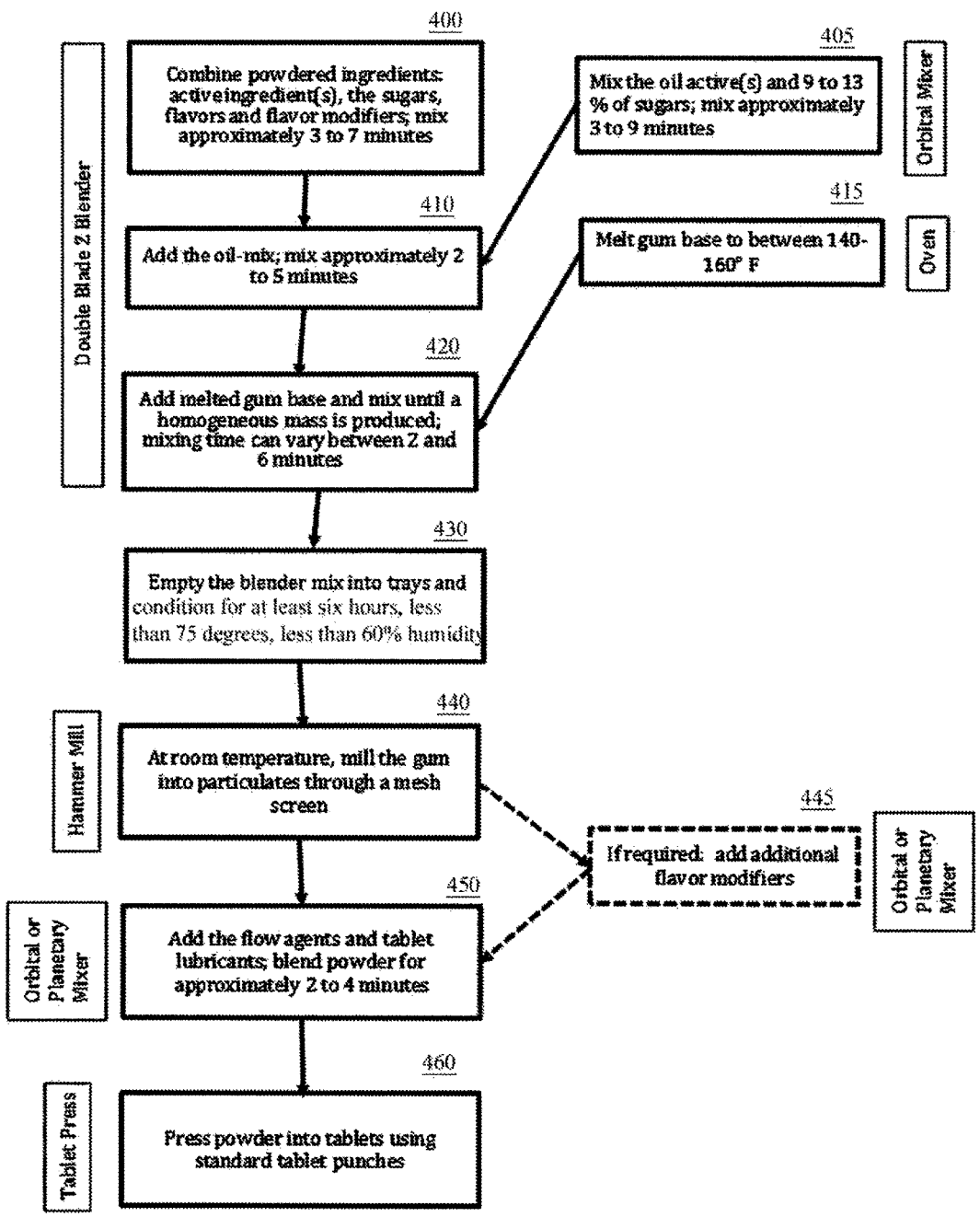
FIG. 4 is a process flow diagram of a fourth embodiment of the method for manufacturing chewing gum according to the invention, suited for active ingredient(s) that are provided in oil form.

FIG. 4 is a flow diagram of a method for manufacturing chewing gum according to an alternate embodiment of the invention suited for active ingredient(s) that are provided in oil form.

At step 405 a pre-mix consisting of the active(s) and a portion of the sweeteners comprising approximately 9 to 13% of one or more sugars (see Tables 2, 4 below) are mixed in a suitable commercial orbital mixer. These ingredients are mixed approximately 3 to 9 minutes, until a homogeneous mix is obtained.

Separately, at step 400 in a double blade Z blender, the balance of the sugars (the remaining 87-91%), plus flavors and flavor modifiers are added and mixed approximately 3 to 7 minutes.

At step 410 the premix containing the active oil(s) is added to the blender and is mixed approximately 2 to 5 minutes.

At step 415 one or more different gum base(s) are placed in trays lined with a sugar and the trays are placed in an oven. The gum base is melted until it reaches an internally measured temperature between 140-160 deg. F.

At step 420 the melted gum base is added into the mixer and mixed until a homogeneous mass is produced. The mixing time may vary within a range of from 2 to 6 minutes.

At step 430 the mass is removed from the blender and conditioned in trays for a minimum of 6 hours at a temperature not greater than 75 deg. F. and 60% relative humidity.

At step 440, after the conditioning period, the gum is milled into particulates at room temperature using a hammer mill that forces the particulates through a mesh screen of appropriate particle size ranging between 0.10 inch to 0.30 inch with an optimal size of 0.24 inch.

Optionally, at step 445 flavor modifiers may be added.

At step 450 the resulting powder is placed in an orbital or planetary mixer and the flow agents and tablet lubricants are added. The powder is blended for approximately 2 to 4 minutes.

At step 460 the powder is tableted using standard tablet punches on any suitable commercial tablet press.

As above this method entirely avoids exposure of the active ingredient to high heat or extreme cold during milling that would otherwise degrade the active's efficacy.

Figure 5:
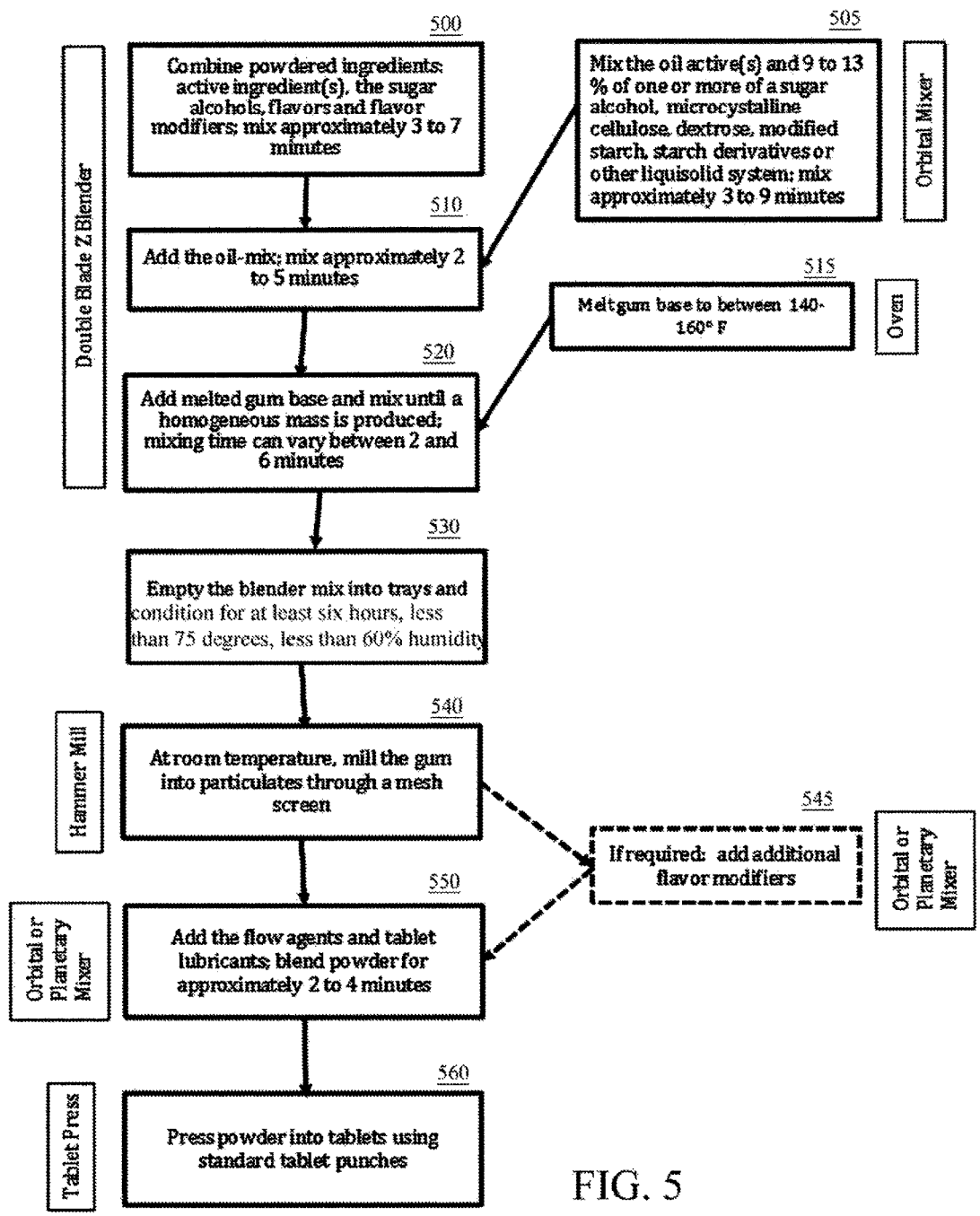
FIG. 5 is a process flow diagram of a fifth embodiment of the method for manufacturing chewing gum according to the invention, suited for active ingredient(s) that are provided in oil form.

FIG. 5 is a flow diagram of a method for manufacturing chewing gum according to an alternate embodiment of the invention suited for active ingredient(s) that are provided in oil form.

At step 505 a pre-mix consisting of the active(s) and a portion of the total sweeteners, e.g., approximately 9 to 13% of one or more of sugar alcohol, microcrystalline cellulose, dextrose, modified starch, starch derivatives or other liqui-solid system (see Table 1, 3, 5, 6 below) are mixed in a suitable commercial orbital mixer. These ingredients are mixed approximately 3 to 9 minutes, until a homogeneous mix is obtained.

Separately, at step 500 in a double blade Z blender, the balance of the sugar alcohols (the remaining 87-91% of the sugar alcohol(s), plus the entirety of the flavors and flavor modifiers are added and mixed approximately 3 to 7 minutes.

At step 510 the premix containing the active oil(s) is added to the blender and is mixed approximately 2 to 5 minutes.

At step 515 one or more different gum base(s) are placed in trays lined with a sugar alcohol and the trays are placed in an oven. The gum base is melted until it reaches an internally measured temperature between 140-160 deg. F.

At step 520 the melted gum base is added into the mixer and mixed until a homogeneous mass is produced. The mixing time may vary within a range of from 2 to 6 minutes.

At step 530 the mass is removed from the blender and conditioned in trays for a minimum of 6 hours at a temperature not greater than 75 deg. F. and 60% relative humidity.

At step 540, after the conditioning period, the gum is milled into particulates at room temperature using a hammer mill that forces the particulates through a mesh screen of appropriate particle size ranging between 0.10 inch to 0.30 inch with an optimal size of 0.24 inch.

Optionally, at step 545 flavor modifiers may be added.

At step 550 the resulting powder is placed in an orbital or planetary mixer and the flow agents and tablet lubricants are added. The powder is blended for approximately 2 to 4 minutes.

At step 560 the powder is tableted using standard tablet punches on any suitable commercial tablet press.

As above this method entirely avoids exposure of the active ingredient to high heat or extreme cold during milling that would otherwise degrade the active's efficacy.

Figure 6:
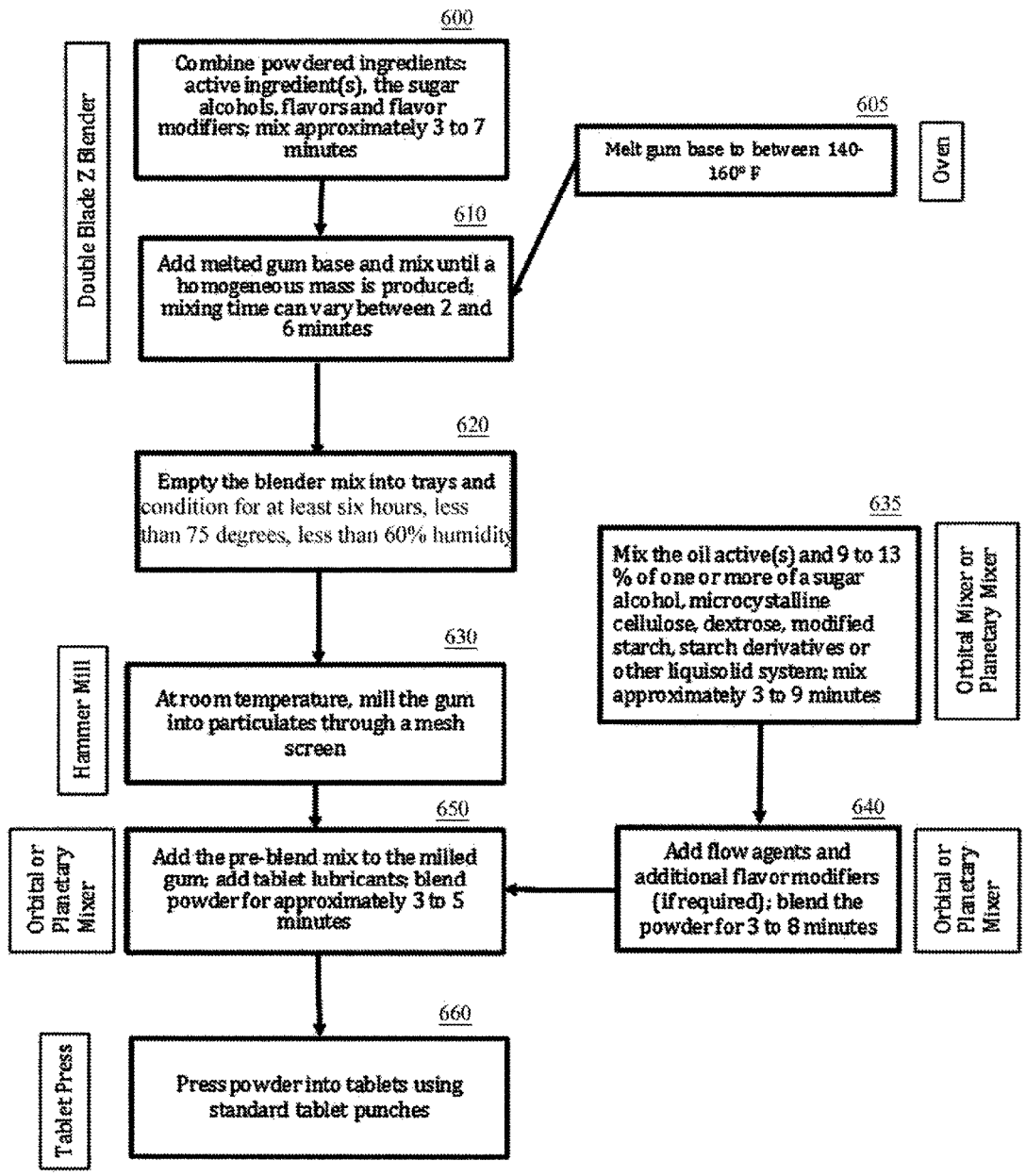
FIG. 6 is a flow diagram of a sixth embodiment of the method for manufacturing chewing gum according to the invention, suited for active ingredient(s) that are provided in oil form.

FIG. 6 is a flow diagram of a method for manufacturing chewing gum according to an alternate embodiment of the invention suited for active ingredient(s) that are provided in oil form.

At step 600 in a double blade Z blender, the sugar alcohols, flavors and flavor modifiers are added and mixed approximately 3 to 7 minutes, and the active oil(s) is added to the blender and is mixed approximately 2 to 5 minutes.

At step 605 one or more different gum base(s) are placed in trays lined with a sugar alcohol and the trays are placed in an oven. The gum base is melted until it reaches an internally measured temperature between 140-160 deg. F.

At step 610 the melted gum base is added into the mixer and mixed until a homogeneous mass is produced. The mixing time may vary within a range of from 2 to 6 minutes.

At step 620 the mass is removed from the blender and conditioned in trays for a minimum of 6 hours at a temperature not greater than 75 deg. F. and 60% relative humidity.

At step 630, after the conditioning period, the gum is milled into particulates at room temperature using a hammer mill that forces the particulates through a mesh screen of appropriate particle size ranging between 0.10 inch to 0.30 inch with an optimal size of 0.24 inch.

At step 635 a pre-mix consisting of the active(s) and approximately 9 to 13% of a portion of the sweeteners, e.g., one or more of sugar alcohol, microcrystalline cellulose, dextrose, modified starch, starch derivatives or other liqui-solid systems (see Table 1, 3, 5, 6 below) are mixed in a suitable commercial orbital or planetary mixer. These ingredients are mixed approximately 3 to 9 minutes, until a homogeneous mix is obtained.

At step 640 the resulting powder is placed in an orbital or planetary mixer, the flow agents and any flavor modifiers are added. The powder is blended for approximately 3 to 8 minutes.

At step 650 the milled gum powder is placed in an orbital or planetary mixer and the pre-mix and tablet lubricants are added. The powder is blended for approximately 3 to 5 minutes.

At step 660 the powder is tableted using standard tablet punches on any suitable commercial tablet press.

As above this method entirely avoids exposure of the active ingredient to high heat or extreme cold during milling that would otherwise degrade the active's efficacy.

Figure 7:
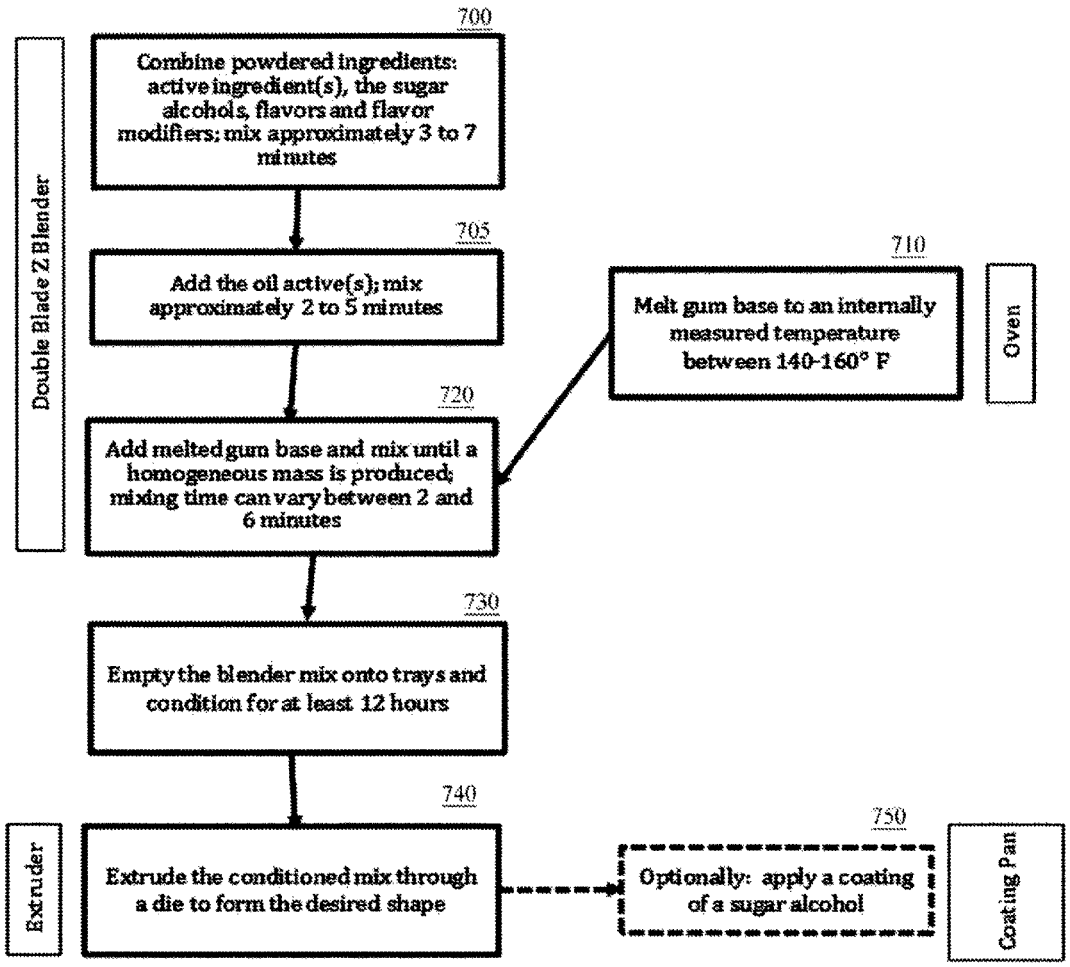
FIG. 7 is a process flow diagram of a seventh embodiment of the method for manufacturing chewing gum according to the invention, suited for active ingredient(s) that are provided in oil form.

FIG. 7 is a flow diagram of a method for manufacturing chewing gum according to an alternate embodiment of the invention suited for active ingredient(s) that are provided in oil form.

At step 700 in a double blade Z blender, the sugar alcohols, flavors and flavor modifiers are added and mixed approximately 3 to 7 minutes.

At step 705 one or more active oil(s) is/are added to the blender and are mixed approximately 2 to 5 minutes.

At step 710 one or more different gum base(s) are placed in trays lined with a sugar alcohol and the trays are placed in an oven. The gum base is melted until it reaches an internally measured temperature between 140-160 deg. F.

At step 720 the melted gum base is added into the mixer and mixed until a homogeneous mass is produced. The mixing time may vary within a range of from 2 to 6 minutes.

At step 730 the mass is removed from the blender and conditioned in trays for a minimum of 12 hours.

At step 740, after the conditioning period, the gum is extruded through a die to form the desired shape of the gum.

Optionally, at step 750 a coating of a sugar alcohol can be applied to the gum piece.

Figure 8:
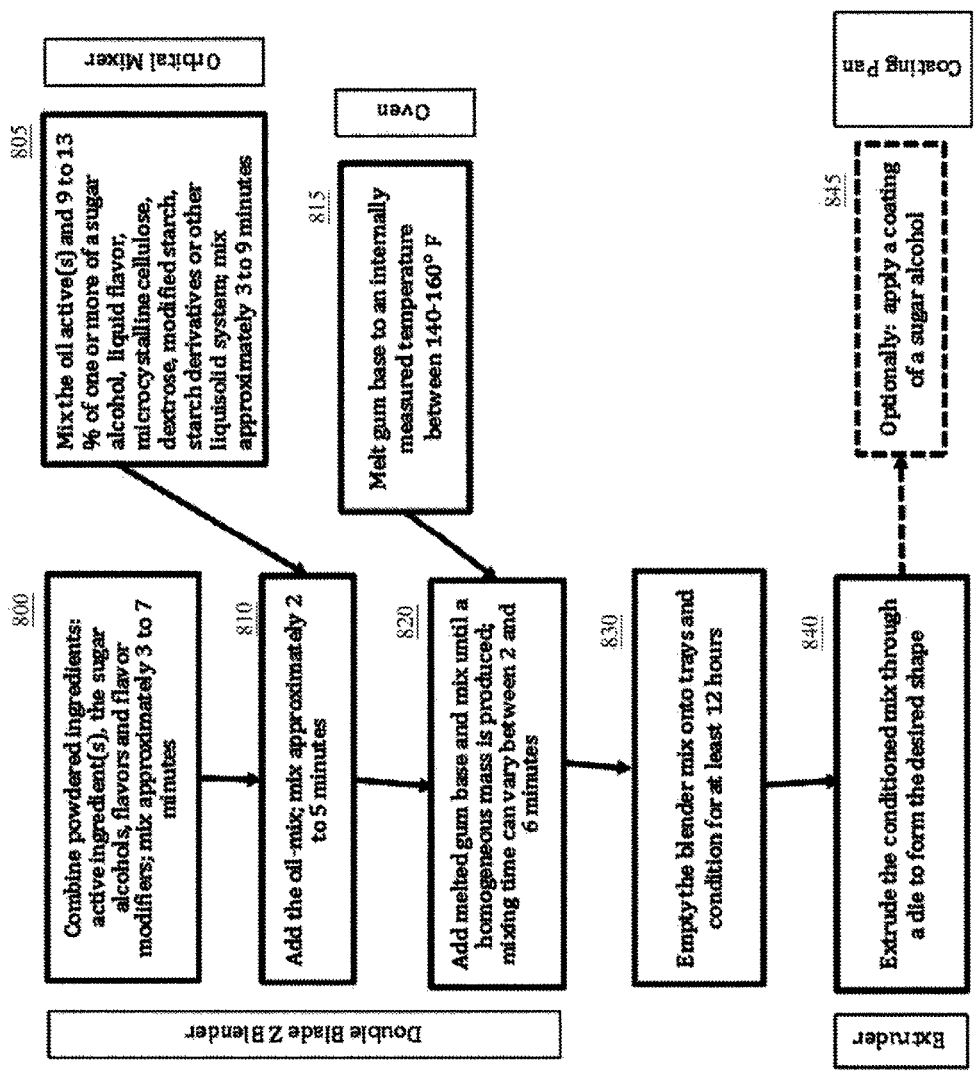
FIG. 8 is a flow diagram of a eighth embodiment of the method for manufacturing chewing gum according to the invention, suited for active ingredient(s) that are provided in oil form.

FIG. 8 is a flow diagram of a method for manufacturing chewing gum according to an alternate embodiment of the invention suited for active ingredient(s) that are provided in oil form.

At step 800 a pre-mix consisting of the active(s) and a portion of the total sweeteners, e.g., approximately 9 to 13% of one or more of sugar alcohol, liquid flavors, microcrystalline cellulose, dextrose, modified starch, starch derivatives or other liquisolid system (see Table 1, 3, 5, 6 below) are mixed in a suitable commercial orbital mixer. These ingredients are mixed approximately 3 to 9 minutes, until a homogeneous mix is obtained.

Separately, at step 805 in a double blade Z blender, the balance of the sugar alcohols (the remaining 87-91% of the sugar alcohol(s), plus the flavors and flavor modifiers are added and mixed approximately 3 to 7 minutes.

At step 810 the premix containing the active oil(s) is added to the blender and is mixed approximately 2 to 5 minutes.

At step 815 one or more different gum base(s) are placed in trays lined with a sugar alcohol and the trays are placed in an oven. The gum base is melted until it reaches an internally measured temperature between 140-160 deg. F.

At step 820 the melted gum base is added into the mixer and mixed until a homogeneous mass is produced. The mixing time may vary within a range of from 2 to 6 minutes.

At step 830 the mass is removed from the blender and conditioned in trays for a minimum of 12 hours.

At step 840, after the conditioning period, the gum is extruded through a die to form the desired shape of the gum.

Optionally, at step 845 a coating of a sugar alcohol can be applied to the gum piece.

As above this method entirely avoids exposure of the active ingredient to high heat or extreme cold that would otherwise degrade the active's efficacy.

The following examples provide specific ingredient listings including a range of acceptable weight % and preferred weight % for ingredients used in the above-described processes for manufacturing particular gums having maximum efficacy.

EXAMPLE 1

Chitosan Chewing Gum

The foregoing method of FIG. 1 has been used successfully to produce a tableted gum with a powdered active ingredient, for example chitosan, using the relative amounts of constituents (sugar alcohol, gum base, flavoring, active ingredient/chitosan, tableting lubricants and powder flow agents, and sweeteners) as shown in Table 1:

TABLE 1

|  | Weight % Range | Optimal Weight % |
|---|---|---|
| A sugar alcohol or a blend of sugar alcohols that can include one or more of the following: sorbitol, isomalt, xylitol, maltitol, mannitol or erythritol | 42.4-75.3 | 64.0 |
| Gum Base | 20.0-30.0 | 25.7 |
| Flavoring in liquid and powder | 2.0-12.0 | 3.3 |
| Active ingredient(s) - chitosan | 1.0-20.0 | 2.5 |
| Tableting lubricants and powder flow agents | 1.5-5.0 | 4.0 |
| Intensive sweeteners | 0.2-0.6 | 0.5 |
| Total |  | 100.0 |

EXAMPLE 2

Caffeine Chewing Gum

The foregoing method of FIG. 2 has been used successfully to produce a tableted gum with a powdered active ingredient, for example caffeine, using the relative amounts of constituents (sugar, gum base, flavoring, active ingredient/caffeine, tableting lubricants and powder flow agents, and sweeteners) as shown in Table 2:

TABLE 2

|  | Weight % Range | Optimal Weight % |
|---|---|---|
| A sugar or a blend of sugars that can include one or more of the following: dextrose, sucrose, fructose, glucose | 55.0-70.0 | 59.6 |
| Gum Base | 20.0-30.0 | 21.2 |
| Flavoring in liquid and powder | 8.0-15.0 | 9.8 |
| Active ingredient(s) - caffeine | 1.0-10.0 | 4.7 |
| Tableting lubricants and powder flow agents | 2.6-5.0 | 3.7 |
| Intensive sweeteners | 0.2-1.5 | 1.0 |
| Total |  | 100.0 |

EXAMPLE 3

Hemp Oil Chewing Gum

The foregoing method of FIG. 3 has been used successfully to produce a tableted gum with an oil-form active ingredient, for example concentrated hemp oil that delivers cannabidiol (CBD) or with a resinous oil that delivers tetrahydrocannabinol (THC). The relative amounts of constituents (sugar alcohol, gum base, flavoring, active ingredient/hemp oil, tableting lubricants and powder flow agents, and sweeteners) as shown in Table 3:

TABLE 3

|  | Weight % Range | Optimal Weight % |
|---|---|---|
| A sugar alcohol or a blend of sugar alcohols that can include one or more of the following: sorbitol, isomalt, xylitol, maltitol, mannitol or erythritol | 48.4-68.8 | 57.8 |
| Gum Base | 20.0-30.0 | 28.5 |
| Flavoring in liquid and powder | 9.0-11.0 | 6.9 |
| Active ingredient(s) - hemp oil | 0.5-10.0 | 2.5 |
| Tableting lubricants and powder flow agents | 1.5-5.0 | 3.8 |
| Intensive sweeteners | 0.2-0.6 | 0.5 |
| Total |  | 100.0 |

EXAMPLE 4

Hemp Oil Chewing Gum

The foregoing method of FIG. 4 has been used successfully to produce a tableted gum with an oil-form active ingredient, for example concentrated hemp oil that delivers cannabidiol (CBD) or with a resinous oil that delivers tetrahydrocannabinol (THC). The relative amounts of constituents (sugars, gum base, flavoring, active ingredient/hemp oil, tableting lubricants and powder flow agents, and sweeteners) as shown in Table 4:

TABLE 4

|  | Weight % Range | Optimal Weight % |
|---|---|---|
| A sugar or a blend of sugars that can include one or more of the following: dextrose, sucrose, fructose, glucose | 53.0-70.0 | 62.9 |
| Gum Base | 20.0-30.0 | 28.6 |
| Flavoring in liquid and powder | 2.5-4.5 | 3.6 |
| Active ingredients(s) - hemp oil | 0.5-10.0 | 0.9 |
| Tableting lubricants and powder flow agents | 1.5-5.0 | 3.5 |
| Intensive sweeteners | 0.2-0.6 | 0.5 |
| Total |  | 100.0 |

EXAMPLE 5

Hemp Oil Chewing Gum

The foregoing method of FIG. 5 has been used successfully to produce a tableted gum with an oil-form active ingredient, for example concentrated hemp oil that delivers cannabidiol (CBD) or with a resinous oil that delivers tetrahydrocannabinol (THC). The relative amounts of constituents (sugar alcohol, cellulose/starch derivatives, gum base, flavoring, active ingredient/hemp oil, tableting lubricants and powder flow agents, and sweeteners) as shown in Table 5:

TABLE 5

|  | Weight % Range | Optimal Weight % |
|---|---|---|
| A sugar alcohol or a blend of sugar alcohols that can include one or more of the following: sorbitol, isomalt, xylitol, maltitol, mannitol or erythritol and one or more of the following: microcrystalline cellulose, dextrose, modified starch, starch derivatives or other liquidsolid system. | 48.4-68.8 | 57.8 |
| Gum Base | 20.0-30.0 | 28.5 |
| Flavoring in liquid and powder | 5.0-11.0 | 6.9 |
| Active ingredient(s) - hemp oil | 0.5-10.0 | 2.5 |
| Tableting lubricants and powder flow agents | 1.5-5.0 | 3.8 |
| Intensive sweeteners | 0.2-0.6 | 0.5 |
| Total |  | 100.0 |

EXAMPLE 6

Hemp Oil Chewing Gum

The foregoing method of FIG. 6 has been used successfully to produce a tableted gum with an oil-form active ingredient, for example concentrated hemp oil that delivers cannabidiol (CBD) or with a resinous oil that delivers tetrahydrocannabinol (THC). The relative amounts of constituents (sugar alcohol, cellulose/starch derivatives, gum base, flavoring, active ingredient/hemp oil, tableting lubricants and powder flow agents, and sweeteners) as shown in Table 6:

TABLE 6

|  | Weight % Range | Optimal Weight % |
|---|---|---|
| A sugar alcohol or a blend of sugar alcohols that can include one or more of the following: sorbitol, isomalt, xylitol, maltitol, mannitol or erythritol and one or more of the following: microcrystalline cellulose, dextrose, modified starch, starch derivatives or other liquisolid system. | 45.0-65.0 | 56.0 |
| Gum Base | 20.0-30.0 | 28.5 |
| Flavoring in liquid and powder | 5.0-11.0 | 9.0 |
| Active ingredient(s) - hemp oil | 0.5-10.0 | 2.5 |
| Tableting lubricants and powder flow agents | 1.5-5.0 | 3.5 |
| Intensive sweeteners | 0.2-0.6 | 0.5 |
| Total |  | 100.0 |

EXAMPLE 7

Hemp Oil Chewing Gum

The foregoing method of FIG. 7 has been used successfully to produce a gum with an oil-form active ingredient, for example concentrated hemp oil that delivers cannabidiol (CBD) or with a resinous oil that delivers tetrahydrocannabinol (THC). The relative amounts of constituents (sugar alcohol, cellulose/starch derivatives, gum base, flavoring, active ingredient/hemp oil, and sweeteners) as shown in Table 7:

TABLE 7

|  | Weight, % Range | Optimal Weight % |
|---|---|---|
| A sugar alcohol or a blend of sugar alcohols that can include one or more of the following: sorbitol, isomalt, xylitol, maltitol, mannitol or erythritol | 45.0-65.0 | 55.5 |
| Gum Base | 25.0-40.0 | 33.0 |
| Flavoring in liquid and powder | 5.0-11.0 | 8.0 |
| Active ingredient(s) - hemp oil | 0.5-10.0 | 3.0 |
| Intensive sweeteners | 0.2-0.6 | 0.5 |
| Total |  | 100.0 |

EXAMPLE 8

Hemp Oil Chewing Gum

The foregoing method of FIG. 8 has been used successfully to produce a gum with an oil-form active ingredient, for example concentrated hemp oil that delivers cannabidiol (CBD) or with a resinous oil that delivers tetrahydrocannabinol (THC). The relative amounts of constituents (sugar alcohol, cellulose/starch derivatives, gum base, flavoring, active ingredient/hemp oil, and sweeteners) as shown in Table 8:

TABLE 8

|  | Weight % Range | Optimal Weight % |
|---|---|---|
| A sugar alcohol or a blend of sugar alcohols that can include one or more of the following: sorbitol, isomalt, xylitol, maltitol, mannitol or erythritol and one or more of the following: liquid flavor, microcrystalline cellulose, dextrose, modified starch, starch derivatives or other liquisolid system. | 45.0-65.0 | 55.5 |
| Gum Base | 25.0-40.0 | 33.0 |
| Flavoring in liquid and powder | 5.0-11.0 | 8.0 |
| Active ingredient(s) - hemp oil | 0.5-10.0 | 3.0 |
| Intensive sweeteners | 0.2-0.6 | 0.5 |
| Total |  | 100.0 |

It should now be apparent that the above described method preserves the efficacy of the active ingredient(s) by avoiding exposure to high heat during mixing, or to extreme cold during milling, either of which can degrade the active's efficacy. Moreover, the active ingredient(s) even when provided in oil form can be mixed directly into the other powder ingredients and tableted, rather than spray-dried onto a powder carrier for tableting as with the prior art methods.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims, and by their equivalents.

What is claimed is:

1. A method for manufacturing chewing gum, comprising the steps of:
    placing one or more gum base(s) in a container with a sugar alcohol in an oven and heating said container until said gum base(s) melts to an internally measured temperature between 140-160 deg. F;
    mixing in a commercial mixer one or more active ingredient(s), sugar alcohol(s) or sugar(s), and flavorings within a range of from 3 to 7 minutes;
    adding the melted gum base into the mixer and mixing within a range of from 2 to 6 minutes until a homogeneous mass is produced;
    conditioning said homogeneous mass for at least 6 hours at a temperature not greater than 75 deg. F and 60% relative humidity;
    milling the dried mass into particulates at room temperature using a mesh screen of appropriate particle size ranging between 0.10 inch to 0.30 inch;
    mixing the particulates with lubricants in an orbital or planetary mixer within a range of from 2 to 4 minutes; and
    tableting the powder by a tablet press,
    wherein the chewing gum comprises at least one therapeutically active ingredient and one or more of sugar(s), sugar alcohol(s), flavoring, tableting lubricants, powder flow agent, sweeteners or combinations thereof.

2. The method according to claim 1, wherein said one or more active ingredient(s) are provided in powdered form.

3. The method according to claim 1, wherein said one or more active ingredient(s) comprise cannabidiol.

4. The method of claim 1, wherein its composition, based on the total weight of the composition, comprises:
    about 45% to 70% by weight of a sugar or a sugar blend
    about 20% to 40% by weight of gum base,
    about 2.5% to 11% by weight of flavoring,
    about 0% to 11% by weight of tableting lubricants and powder flow agents,
    about 0.2% to 0.6% by weight of high-intensity sweeteners,
    about 0.5% to 10% by weight of the active ingredient, or combinations thereof.

5. The method of claim 1, wherein the active ingredient is hemp oil.

6. The method of claim 5, wherein the hemp oil comprises cannabidiol (CBD).

7. The method of claim 5, wherein the hemp oil is a resinous oil comprising tetrahydrocannabinol (THC).

8. The method of claim 1, wherein the method of claim 1 comprises sugar alcohols, said sugar alcohols comprising sorbitol, isomalt, xylitol, mannitol, erythritol, or combinations thereof.

9. The method of claim 1, wherein the method of claim 1 comprises sugars, said sugars comprising dextrose, sucrose, fructose, glucose, or combinations thereof.

10. The method of claim 1, wherein the sugars comprise microcrystalline cellulose, dextrose, modified starch, starch derivatives, or combinations thereof.

* * * * *